US007867527B2

(12) United States Patent
Charles nee Newsham et al.

(10) Patent No.: US 7,867,527 B2
(45) Date of Patent: Jan. 11, 2011

(54) **SKIN LIGHTENING COMPOSITIONS COMPRISING GOYA (*MOMORDICA CHARANTIA*) AND PINE EXTRACT**

(75) Inventors: Rebecca Louise Charles nee Newsham, Shambrook (GB); Paula Rachel Yates, Eaton Bray (GB)

(73) Assignee: Conopco, Inc., Englewood Cliffs, NJ (US)

( * ) Notice: Subject to any disclaimer, the term of this patent is extended or adjusted under 35 U.S.C. 154(b) by 533 days.

(21) Appl. No.: 11/547,553

(22) PCT Filed: Feb. 18, 2005

(86) PCT No.: PCT/EP2005/001821

§ 371 (c)(1), (2), (4) Date: Dec. 17, 2007

(87) PCT Pub. No.: WO2005/094774

PCT Pub. Date: Oct. 13, 2005

(65) Prior Publication Data

US 2008/0268079 A1 Oct. 30, 2008

(30) Foreign Application Priority Data

Mar. 29, 2004 (EP) ................................. 04251836

(51) Int. Cl.
*A61K 36/13* (2006.01)
*A61K 36/00* (2006.01)
*A61K 9/00* (2006.01)
*A61K 47/00* (2006.01)

(52) U.S. Cl. ....................... 424/770; 424/725; 424/400; 424/439

(58) Field of Classification Search ....................... None
See application file for complete search history.

(56) References Cited

U.S. PATENT DOCUMENTS

| | | | | |
|---|---|---|---|---|
| 4,663,157 | A | 5/1987 | Brock | |
| 5,470,874 | A | 11/1995 | Lerner | |
| 5,602,259 | A | 2/1997 | Boo et al. | |
| 5,916,915 | A * | 6/1999 | Hong et al. | 514/474 |
| 6,497,860 | B1 * | 12/2002 | Kawato et al. | 424/62 |

FOREIGN PATENT DOCUMENTS

EP 0 692 243 A 1/1996

OTHER PUBLICATIONS

DW ACC 1994-089259, Feb. 1994, JP or Derwent, Nakaguchi.*
DW ACC 2001-495315, Mar. 2001, KR or Derwent, Lee et al.*
DW ACC 2004-229990, Oct. 2003, Derwent or JP 2, Tomita.*
International Search Report No. PCT/EP2005/001821 mailed Mar. 13, 2006.
Frank Schonlau: "The Cosmeceutical Pycnogenol" J. Appl. Cosmetol., vol. 20, 2002, pp. 241-246, XP009036077.

* cited by examiner

*Primary Examiner*—Christopher R Tate
*Assistant Examiner*—Randall Winston
(74) *Attorney, Agent, or Firm*—Michael P. Aronson

(57) ABSTRACT

A skin lightening composition comprising Goya or an extract thereof, and pine bark extract.

12 Claims, No Drawings

SKIN LIGHTENING COMPOSITIONS COMPRISING GOYA (*MOMORDICA CHARANTIA*) AND PINE EXTRACT

FIELD OF THE INVENTION

The present invention relates to agents for skin lightening, the use of these agents for inhibiting the production of melanin in the skin of a mammal and compositions suitable for such use.

BACKGROUND TO THE INVENTION

Some people with naturally darker skin types desire to induce a degree of lightening in their overall skin colour. Skin colour is determined primarily by the amount and type of melanin, a substance which is produced within the skin by melanocytes which reside in the epidermis. Melanin is present in two forms, namely dark melanin and light melanin. Skin lightening would result if the production of dark melanin were reduced and/or the ratio of light melanin to dark melanin production were increased.

SUMMARY OF THE INVENTION

We have now found that a combination of an extract of the vegetable Goya with extract of pine bark synergistically reduces dark melanin production.

Accordingly, the present invention provides a skin lightening composition comprising Goya, or an extract thereof, and a pine bark extract.

The present invention also provides a method of inhibiting the production of melanin in the skin of a mammal, the method comprising administering to said human an effective amount of Goya or an extract thereof and pine bark extract.

In a related aspect, the present invention further provides Goya, or an extract thereof, and pine bark extract for use in inhibiting the production of melanin in the skin of a mammal.

The present invention further provides a method of increasing the ratio of light melanin to dark melanin in the skin of a mammal, the method comprising administering to said mammal, an effective amount of Goya, or an extract thereof, and a pine bark extract.

The present invention also provides Goya, or an extract thereof, and pine bark extract for use in increasing the ratio of light melanin to dark melanin in the skin of a mammal.

In another aspect the present invention provides the use of Goya, or an extract thereof, and pine bark extract in the manufacture of a composition for inhibiting the production of melanin and/or increasing the ratio of light melanin to dark melanin in the skin of a mammal.

The present invention also provides a method of inhibiting in the skin of an individual, the transport of melanin from melanocytes to keratinocytes, which method comprises administering to said individual an effective amount of Goya, or an extract thereof, and a pine bark extract.

DETAILED DESCRIPTION OF THE INVENTION

Unless defined otherwise, all technical and scientific terms used herein have the same meaning as commonly understood by one of ordinary skill in the art.

Compositions and Product Forms

Compositions of the invention comprise whole Goya, or an extract thereof, and pine bark extract. Goya (*Momordica charantia*) is also known as bitter melon.

An extract differs from the whole plant materials from which it is derived in that the various components present in the whole vegetable will be present in different amounts in the extract, or substantially absent.

Extracts of plant materials are typically made by solvent extraction. Plant materials may be subject to mechanical treatment, such as grinding, prior to extraction. Solvents include "solvent" includes polar and non-polar organic solvents, water, and mixtures thereof. Preferred solvents are acetone, water, ethanol and mixtures thereof. Extraction procedures may include a heating step. Solvent extracted components may be subject to further purification/separation steps such as chromatography or fractional distillation. As used herein, "fraction" means any fractioned part of a solvent containing one or more Goya/pine bark ingredients, e.g. obtained by chromatography or by fractional distillation.

Preferably the pine bark extract is an extract of the bark of French maritime pine (*Pinus pinatus*). One such preferred extract is available commercially as Pycnogenol™.

The compositions of the present invention may be provided in forms for topical and/or systemic administration. For example, both the Goya and pine bark extract may be dosed systemically or both topically or one may be dosed systemically and the other topically, e.g. Goya could be delivered systemically and the pine bark extract topically or vice versa. The Goya component may comprise two or more different fractions or products of two or more different extraction processes. These may be all dosed systemically or all topically, or respectively split between topical and systemic delivery forms. Similarly, the pine bark extract may comprise two or more different fractions or products of two or more different extraction processes. These may also be all dosed systemically or all topically, or respectively split between topical and systemic delivery forms. Preferably, where the Goya and pine bark extract are provided in separate dosage forms, the dosage form comprising the pine bark extract lacks Goya, and vice-versa.

Thus, the term "composition" as used herein in the context of a composition according to the present invention refers both to unitary compositions containing all essential ingredients. However, the term also covers the situation where individual components of the overall composition, i.e. the Goya and the pine bark extract are split between two different compositional forms which are supplied together as a product. For example, a product may comprise one compositional form for systemic delivery of its component(s) and one compositional form for topical delivery of its component(s). Examples of products containing combinations of such compositional forms are a skin cream and a nutritional supplement tablet.

Topical Compositions

In one embodiment, the compositions of the invention are formulated for topical administration, i.e. the composition is in the form of a topical composition. Accordingly, the compositions of the invention can be administered topically to a subject, i.e., by the direct laying on or spreading of the composition on skin. Such compositions can be prepared by combining a safe and effective amount of the active substance or substances as described above with a pharmaceutically-acceptable topical carrier or diluent, i.e. a dermatologically acceptable carrier or diluent.

The composition typically contains from about 0.01% to about 35% by weight of each of the active ingredients, preferably from about 0.1 wt % to about 35 wt %, more preferably from about 1 wt % to about 35 wt %, such as from 5 or 10 wt % to about 25 wt %.

The topical compositions useful in this invention may be made into a wide variety of product types. These include, but are not limited to lotions, creams, gels, sticks, sprays, ointments and pastes. These product types may comprise several types of carrier systems including, but not limited to solutions, emulsions, gels and solids.

The topical compositions useful in this invention formulated as solutions typically include a pharmaceutically-acceptable aqueous or organic solvent. The terms "pharmaceutically-acceptable aqueous solvent" and "pharmaceutically-acceptable organic solvent" refer to a solvent which is capable of having dispersed or dissolved therein the active(s), and possesses acceptable safety properties (e.g., irritation and sensitisation characteristics). Examples of suitable organic solvents include: propylene glycol, polyethylene glycol (200-600), polypropylene glycol (425-2025), poly vinyl pyrrolidine, propylene glycol-14 butyl ether, glycerol, 1,2,4-butanetriol, sorbitol esters, 1,2,6-hexanetriol, ethanol, isopropanol, butanediol, and mixtures thereof. These solutions preferably contain from about 0.1 wt % to about 20 wt %, more preferably from about 1 wt % to about 20 wt % more preferably still from about 1 wt % to about 10 wt %, of each active.

If the topical compositions useful in this invention are formulated as an aerosol and applied to the skin as a spray-on, a propellant is added to a solution composition.

Topical compositions may be formulated as a solution comprising an emollient, i.e. a material used for the prevention or relief of dryness, as well as for the protection of the skin. A wide variety of suitable emollients are known and may be used herein (see Sagarin, Cosmetics, Science and Technology 2nd Edition, Vol. 1, pp. 32-43 (1972)). Such compositions preferably contain from about 2% to about 50% of a topical pharmaceutically-acceptable emollient.

If the carrier is formulated as an emulsion, preferably from about 1% to about 10%, more preferably from about 2% to about 5%, of the carrier system comprises an emulsifier. Emulsifiers may be non-ionic, anionic or cationic. Suitable emulsifiers are disclosed in, for example, McCutcheon's Detergents and Emulsifiers, North American Edition, pages 317-324 (1986).

Single emulsion skin care preparations, such as lotions and creams, of the oil-in-water type and water-in-oil type are well known in the cosmetic art. Such emulsions can stabilise and enhance the penetration of actives. Multiphase emulsion compositions, such as the water-in-oil-in-water type may also be used. In general, such single or multiphase emulsions contain water, emollients and emulsifiers as essential ingredients.

Another emulsion carrier system that can be used is a micro-emulsion carrier system. Such a system comprises from about 91% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other non-ionics; and from about 7% to about 20% water.

Liposomal formulations can also be used. These formulations can stabilise actives and also improve delivery of actives which do not penetrate well. Such compositions can be prepared by first combining the active with a phospholipid, such as dipalmitoylphosphatidyl choline, cholesterol and water according to the method described in Mezei & Gulasekharam, Journal of Pharmaceutics and Pharmacology, Vol. 34 (1982), pp. 473-474, or a modification thereof. Epidermal lipids of suitable composition for forming liposomes may be substituted for the phospholipid. The liposome preparation is then incorporated into one of the above topical carrier systems (for example, a gel or an oil-in-water emulsion) to produce the liposomal formulation. Other compositions and cosmetic/pharmaceutical uses of topically applied liposomes are described in Mezei, M., "Liposomes as a Skin Drug Delivery System"; Topics in Pharmaceutical Sciences (D. D. Breimer and P. Speiser, eds.), Elsevier Science Publishers B. V., New York, N.Y., 1985, pp. 345-358.

If the topical compositions are formulated as a gel or a cosmetic stick, such compositions can be formulated by the addition of a suitable amount of a thickening agent to a cream or lotion formulation.

Topical compositions may also be formulated as makeup products, such as foundations. Foundations are solution or lotion-based with appropriate amounts of thickeners, pigments and fragrance.

Various water-soluble materials may also be present in the compositions. These include humectants, proteins and polypeptides and preservatives. In addition, the topical compositions useful herein can contain conventional cosmetic adjuvants, such as dyes, opacifiers (e.g., titanium dioxide), pigments and perfumes.

The topical compositions useful in this invention may also include a safe and effective amount of a penetration enhancing agent. A preferred amount of penetration enhancing agent is from about 1% to about 5% of the composition. Examples of useful penetration enhancers are described in U.S. Pat. No. 6,068,834. Other conventional skin care product additives may also be included in the compositions. For example, collagen, hyaluronic acid, elastin, hydrolysates, primrose oil, jojoba oil, epidermal growth factor, soybean saponins, mucopolysaccharides, and mixtures thereof may be used.

It may be desirable to include in the compositions of the invention, one or more sun screening agents. A wide variety of conventional sun screening agents are disclosed in, for example, Cosmetics, Science and Technology 2nd Edition (1972), Vol. 1, Chapter VIII, pages 189 et seq. See also U.S. Pat. No. 6,068,834.

The sun screening agent must be compatible with the active(s). The composition preferably comprises from about 1% to about 20%, more preferably from about 2% to about 10%, of a sun screening agent. Exact amounts will vary depending upon the sunscreen chosen and the desired Sun Protection Factor (SPF).

An agent may also be added to any of the compositions of the invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157.

The present invention relates to methods of inhibiting melanin production in the skin of a mammal, typically a human. In one embodiment, such methods comprise the administration of a safe and effective amount of a composition of the invention to the skin or regions thereof the skin. The amount of active agent and frequency of application will vary depending on the initial condition of the skin and the desired end result. Generally, the compositions should be administered in a sufficient amount and for a sufficient period of time to visibly whiten the skin.

Any dose which is less than the toxic level may be used, thus it is contemplated that for certain dosage forms, particularly topical dosage forms, the "dose" is any amount that provides the desired effect, and that amount may be so large due to frequency of application and amount applied that the maximum effective amount is irrelevant.

A safe and effective amount of active in a topical composition is applied, generally from about 1 μg to about 1 mg per $cm^2$ skin per application, preferably from about 2 μg to about 800 $\mu g/cm^2$ skin per application, more preferably from about 30 μg to about 700 $\mu g/cm^2$ skin, most preferably from about 75 μg to about 250 $\mu g/cm^2$ skin. Frequency of application typically ranges from about four times a day to about twice a week, more preferably from about three times a day to about once every other day, more preferably at least twice daily. It is generally preferred that at least one application occurs in the evening.

Systemic Compositions

Compositions of the invention can be combined with a pharmaceutically acceptable carrier or diluent to produce a pharmaceutically composition. Pharmaceutically acceptable diluents or carriers suitable for use in such compositions are well known in the art of pharmacy. The compositions of the invention typically contain from 0.1 to 35% by weight of each active, such as from 1 to 25% by weight of active, more preferably at least 5 or 10 wt % of active.

The pharmaceutical composition may consist of solid dosage forms such as tablets, hard gelatin capsules, soft gelatin capsules, bulk powders, and microcapsules of the drug. Alternately, it may consist of a liquid dosage form such as an aqueous or nonaqueous solution, emulsion, or suspension.

Solid compositions for oral administration are preferred compositions of the invention. Solid compositions of the invention are preferably prepared in unit dosage form, such as in the form of tablets and capsules. Suitably tablets may be prepared by mixing the active combination with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly, capsules, for example hard or soft gelatin capsules, containing the active combination optionally in the form of beads with or without added excipients, may be prepared by conventional means and, if desired, provided with enteric coatings in a known manner. The tablets may be formulated in a manner known to those skilled in the art so as to give a controlled release of the compound of the present invention.

Controlled release forms of the pharmaceutical compositions of the present invention include rapid release formulations such as soluble granules or melt filled fast release capsules, delayed release formulations such as tablets provided with enteric coatings, for example, of cellulose acetate phthalate and, in particular, sustained release formulations. Numerous types of sustained release formulations are known to those skilled in the art. Typically, the active combination may be encapsulated within a release retarding coating, for example, a copolymer of cellulose ether and acrylate, or may be bound to small particles such as, for example, ion exchange resin beads. Alternatively, the active combination may be incorporated into a matrix containing a release retarding agent such as a hydrophilic gum e.g. xanthan gum, a cellulose derivative eg. hydroxypropyl methylcellulose, or a polysaccharide, wax or plastics material.

The active combination may be formulated into a solid dosage form in which the two active ingredients are kept separate. For example, the dosage form may be a bilayer tablet in which the active ingredients are contained in different layers. The different layers can be formulated so as to provide the optimum release profile for each drug.

Liquid fill compositions for example viscous liquid fills, liquid paste fills or thixotropic liquid fills are also suitable for oral administration. Melt filled compositions may be obtained by mixing the active combination with certain esters of natural vegetable oil fatty acids, for example, the Gelucire™ range available from Gattefosse to provide a variety of release rates. Suitably a melt-filled capsule comprises from 10 to 80% total active and from 20 to 90% of a fatty acid ester excipient which comprises one or more polyol esters and triglycerides of natural vegetable oil fatty acids.

Preferably oral liquid compositions comprise from 1 to 5 wt % of each active together with from 1 to 50 wt % of a diluent, the remainder made up with sterile water. Optionally the composition may contain suspending agents, thickeners, cosolvents such as alcohol and/or preservatives. Suitable diluents include sweetening agents for example sorbitol, xylitol or sucrose. Suitable suspending agents or thickeners include cellulose gums, agar or natural gums, for example xanthan gum. Flavourings or other taste-masking agents known to those skilled in the art for example saccharin, sodium saccharin, acesulpham K or aspartame may be added.

Compositions of the invention suitable for parenteral administration can be prepared by combination of the active with known pharmaceutical forms for such administration, for example sterile suspensions or sterile solutions of the active in a suitable solvent such as saline.

The preferred mode of administration is orally.

Generally, the compositions should be administered in a sufficient amount and for a sufficient period of time to visibly whiten the skin.

The amount of the compound administered depends upon the bioavailability of the compound from the pharmaceutical composition, in particular where oral administration is used. Typically, however, the compounds of this invention are dosed in an amount of from about 0.01 mg/kg of body weight to about 100 mg/kg, preferably from about 0.1 to about 30 mg/kg of body weight. The amount of the pharmaceutical composition depends upon the percent of compound within its formula, which is a function of the amount of the compound required per dose, its stability, release characteristics and other pharmaceutical parameters. The doses are typically administered from once or twice weekly to one or twice daily.

The routes of administration and dosages described are intended only as a guide since a skilled practitioner will be able to determine readily the optimum route of administration and dosage for any particular individual.

Another means of systemic dosing comprises dosing any of the aforementioned compositions in a food product which does not therefore necessarily require use of a pharmacologically acceptable carrier.

As used herein, the term "food products" includes both food products as such and beverages. Suitable food products as such include spreads, dairy products (including milk and yoghurts), desserts, convenience foods/snacks, breakfast cereals and cereal bars, ready-cook meals, bread and frozen confections such as ice creams, water ices and sorbets and yoghurt ice creams. Food products also include dietary/nutritional supplements. Suitable beverages include tea, tea-flavoured drinks, coffee, soft drinks (e.g. carbonated squashes etc) and fruit juice.

The food products are typically supplemented with the active ingredients of the invention so that they contain higher amounts of the active ingredient(s) than they would normally contain.

Where the Goya, or extract thereof, and/or pine bark extract are split between topical and systemic regimes, the upper and lower values of the optimum daily dosage ranges are proportioned according to the split between topical and systemic as appropriate.

Uses

The compositions of the invention can be used to modulate melanin production in the skin of a mammal, in particular a human. More specifically, they can be used to increase the ratio of light melanin:dark melanin in skin, for example by inhibiting the production of dark melanin (eumelanin) in skin. Preferably the ratio of light melanin:dark melanin is increased at least 1.5-fold relative to the control (measured as the percentage of light melanin relative to the control divided by the percentage of dark melanin relative to the control e.g. if light melanin is increased to 150% of the control and dark melanin is decreased to 50% of the control, the ratio is 3:1 relative to the control). Consequently, the compositions of the invention can be used to induce skin lightening in mammals such as humans. The advantage of increasing the ratio of light melanin:dark melanin in skin rather than simply inhibiting production of both types of melanin is that a better skin tone is produced.

The present invention will now be described further with reference to the following examples which are illustrative only and non-limiting.

EXAMPLES

In these examples, evaluation of the ability of Goya and Pycnogenol to influence levels of dark and light melanin were tested using the commercially available Melanoderm™ system.

Goya extract was prepared by freezing samples to −80° C. and grinding in a coffee grinder. The sample was then freeze-dried overnight and Soxhlet extracted for 16 hours with 200 ml acetone. The extract was then rotary evaporated at 40° C. under vacuum, and the concentrated residue dried under a stream of nitrogen. Samples were then stored under nitrogen at −20° C.

Pycnogenol was obtained from Solgar (Pycnogenol® 30 mg)

Treatment Regime for Melanoderms™

The MelanoDerm™ MatTeks system consists of normal, human-derived epidermal keratinocytes (NHEK) and melanocytes (NHM) which have been cultured to form a multi-layered, highly differentiated model of the human epidermis. The NHM within co-cultures undergo spontaneous melanogenesis leading to tissues of varying levels of pigmentation. The tissues are produced using serum free medium without artificial stimulators of melanogenesis such as TPA and IBMX. The cultures are grown on cell culture inserts at the air-liquid interface, allowing for simulated topical application of agents to be tested. Introduction of agents into the medium simulates systemic application. Thus, the model provides a useful in vitro means to evaluate agents designed to modulate skin pigmentation.

On delivery, the melanoderms (MatTek MEL-300-B) were placed onto metal ring supports in a 6 well plate containing 5 ml of pre-warmed maintenance media (of EPI-100-MM-PRF), using asceptic technique as per MatTek's protocol. Incubation was carried out overnight at 37° C. and 4% $CO_2$ to allow the melanoderms to recover and equilibrate fully. Once placed under these conditions the MEL-300 tissue, undergo melanogenesis and differentiation.

Treatment was initiated on the following morning. Agents to be tested were dissolved in appropriate solvents and added to warmed media at final concentrations pre-assessed for melanocyte toxicity. Each time the media was changed, the spent media was aspirated from the melanoderms and reserved for testing for toxicity (Lactate Dehydrogenase (Promega)) and Interleukin-1 release (R&D systems) and replaced with a fresh dose of media plus test agents whether within the media of the melanoderm. Melanoderms were returned to the incubator. This treatment regime was repeated every 48 hours until a relative difference in darkening was observed between control and test agents.

On observation of differences in darkening, microscopic and macroscopic darkening were recorded photographically. Harvesting the tissue of the melanoderm involved cutting away the tissue from its plastic support and was followed by quantification of melanin present post-treatment versus untreated.

Selective Solubilisation of Melanin from Melanoderm Tissue (1) Quantification of Alkali-soluble Melanin (Light Melanin)

Melanoderm samples were cut from the plastic holders and the wet weight of tissue measured. 200 μl 1M NaOH/8M urea was added to the melanoderm sample the tissue homogenised in a microfuge tube. Samples were whirlmixed at RT for 30 minutes on and off to release the soluble melanin. Samples were centrifuged at 13,000 rpm for 10 minutes and supernatant containing soluble melanin was removed to a fresh tube.

Protein was extracted from the supernatant by addition of 200 μl chloroform and then by mixing vigorously for 1 minute. Phases were separated by centrifugation at 13,000 rpm for 10 minutes. 150 μl of supernatant was added to a microtitre plate (in duplicate) and the OD 340 nM ascertained.

(2) Quantification of Alkali-insoluble Melanin (Dark Melanin)

1M NaOH was added to the remaining pellet which contains the insoluble melanin and the sample vortexed for one minute. The sample was then incubated in a water bath at 37° C. for 96 hrs with daily mixing to released the insoluble melanin. The sample was centrifuged for 10 minutes at 13,000 rpm with 200 μl of chloroform and 190 μl of the supernatant taken to a fresh tube. The supernatant was centrifuged again and 150 μl removed to a microtitre plate for analysis of absorption at 340 nm.

Calculation of Absolute Melanin Concentration

Absolute melanin is calculated as the actual melanin quantity calculated from a previously determined light melanin standard curve:

$x=(y-0.003)/4.76423$ (where $x$=concentration of melanin and $y$=optical density at 340 nm).

For dark melanin, the curve is $x=(y-0.00553)/3.70312$.

Results

| | Change in Total Melanin μg/g | Change in Light Melanin μg/g | Change in Dark Melanin μg/g | Ratio of light melanin (μg/g): dark melanin (μg/g) |
|---|---|---|---|---|
| Control | — | — | — | 0.049 |
| Pycnogenol 10 μg/ml | −0.39 | +0.28 | −0.67 | 0.064 |
| Goya 10 μg/ml | +0.38 | +0.39 | −0.01 | 0.066 |

-continued

| | Change in Total Melanin μg/g | Change in Light Melanin μg/g | Change in Dark Melanin μg/g | Ratio of light melanin (μg/g): dark melanin (μg/g) |
|---|---|---|---|---|
| Pycnogenol 10 μg/ml + Goya 10 μg/ml | −1.82 | +0.43 | −2.25 | 0.077 |

Treatment with a combination of Goya and Pyconogenol reduced the total melanin produced by the melanoderm to a much greater extent than either ingredient individually. Soluble melanin was increased in all cases and insoluble melanin was decreased to a substantially greater extent by treatment with a combination of Goya and Pycnogenol as compared with either ingredient individually. When the ratio of soluble melanin:insoluble melanin was calculated, for Goya and Pycnogenol combined, there was a 50% increase in the ratio compared to the control ratio.

These results indicate that the combination inhibits dark melanin production in a synergistic manner without inhibiting light melanin production—indeed there was an increase in light melanin production in all cases.

The various features and embodiments of the present invention, referred to in individual sections above apply, as appropriate, to other sections, *mutatis mutandis*. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. A skin lightening composition comprising Goya or an extract thereof, and an aqueous extract of pine bark, wherein the Goya or extract thereof is present in an amount of from about 10 to about 35 wt % of the composition, and wherein the aqueous extract of pine bark is present in an amount of from about 10 to about 35 wt % of the composition.

2. A skin lightening composition according to claim 1, wherein the composition is formulated for systemic administration.

3. A skin lightening composition according to claim 1, wherein the composition is formulated for topical administration.

4. A skin lightening composition according to claim 3, wherein the Goya or extract thereof is present in an amount of from about 1 to about 35 wt % of the composition.

5. A skin lightening composition according to claim 1, wherein the aqueous extract of pine bark is present in an amount of from about 1 to about 35 wt % of the composition.

6. A method of inhibiting the production of melanin in the skin of a human who desires to induce a degree of lightening in their overall skin color, the method comprising administering to said human an effective amount of the composition according to claim 1.

7. A method according to claim 6 wherein the composition is administered systemically or topically.

8. A method of increasing the ratio of light melanin to dark melanin in the skin of a human who desires to induce a degree of lightening in their overall skin color, the method comprising administering to said human an effective amount of the composition according to claim 1.

9. A method of inhibiting in the skin of an individual, the transport of melanin from melanocytes to keratinocytes, which method comprises administering to said individual an effective amount of the composition according to claim 1.

10. The skin lightening composition according to claim 1, wherein the composition produces at least a 1.5 fold increase in a ratio of light melanin to dark melanin when tested in-vitro utilizing a cell culture consisting of normal, human-derived epidermal keratinocytes (NHEK) and melanocytes (NHM) which have been cultured to form a multilayered, highly differentiated model of the human epidermis.

11. The method according to claim 6 wherein the effective amount produces at least a 1.5 fold increase in a ratio of light melanin to dark melanin when tested in-vitro utilizing a cell culture consisting of normal, human-derived epidermal keratinocytes (NHEK) and melanocytes (NHM) which have been cultured to form a multilayered, highly differentiated model of the human epidermis.

12. The method according to claim 8 wherein the effective amount produces at least a 1.5 fold increase in the ratio of light melanin to dark melanin when tested in-vitro utilizing a cell culture consisting of normal, human-derived epidermal keratinocytes (NHEK) and melanocytes (NHM) which have been cultured to form a multilayered, highly differentiated model of the human epidermis.

* * * * *